United States Patent [19]

Stolowitz

[11] Patent Number: 5,668,257

[45] Date of Patent: Sep. 16, 1997

[54] PHENYLBORONIC ACID COMPLEXING REAGENTS DERIVED FROM AMINOLALICYLIC ACID

[75] Inventor: Mark L. Stolowitz, Long Beach, Calif.

[73] Assignee: Prolinx, Inc., Bothell, Wash.

[21] Appl. No.: 482,883

[22] Filed: Jun. 7, 1995

Related U.S. Application Data

[62] Division of Ser. No. 188,531, Jan. 28, 1994, Pat. No. 5,594,151.

[51] Int. Cl.⁶ .................... C07C 331/28; C07C 233/65
[52] U.S. Cl. .................... 530/391.1; 424/450; 530/345; 530/350; 530/391.7; 530/402; 530/409; 536/17.1; 558/17; 560/315; 562/26; 562/453; 562/622; 562/624; 564/74; 564/158; 564/213; 564/214; 564/220; 564/246
[58] Field of Search ................. 558/17; 560/315; 562/26, 453, 622, 624; 564/74, 158, 213, 214, 220, 246; 530/345, 350, 391.1, 391.7, 402, 409; 424/450; 536/17.1

[56] References Cited

U.S. PATENT DOCUMENTS

| | | | |
|---|---|---|---|
| 2,548,257 | 7/1951 | Goldberg et al. | 562/453 |
| 4,269,605 | 5/1981 | Dean et al. | 436/67 |
| 4,281,181 | 7/1981 | Nagasawa et al. | 562/453 |
| 4,496,722 | 1/1985 | Gallop et al. | 544/69 |
| 4,713,346 | 12/1987 | Gallop et al. | 436/86 |
| 4,783,487 | 11/1988 | Brune | 514/563 |
| 4,851,443 | 7/1989 | Brune | 514/563 |
| 4,894,229 | 1/1990 | Polson et al. | 424/92 |
| 4,910,300 | 3/1990 | Urdea et al. | 536/287 |
| 5,002,883 | 3/1991 | Bieniarz et al. | 435/176 |
| 5,045,451 | 9/1991 | Uhr et al. | 435/6 |
| 5,093,232 | 3/1992 | Urdea et al. | 435/7.23 |
| 5,183,653 | 2/1993 | Linder et al. | 424/1.1 |

FOREIGN PATENT DOCUMENTS

| | | |
|---|---|---|
| 9013818 | 11/1990 | WIPO. |
| 9208722 | 5/1992 | WIPO. |
| 9420858 | 9/1994 | WIPO. |

OTHER PUBLICATIONS

Wilcheck, M. & Bayer, E.A.;"introduction to Avidin–Biotin Technology"; *Methods in Enzymology;* vol. 184; 1990 (USA).
Kessler et al.; "Non–radioactive Labeling and Detection of Nucleic Acids"; *Biol. Chem. Hoppe–Seyler;* vol. 371, pp. 917–927; 1990 (USA).
Singhal, R.P. & DeSilva, S.S.M.; "Boronate Affinity Chromatography"; *Advances in Chromatography;* vol. 31, pp. 293–335; 1992 (USA).
Mazzeo, J.R. & Krull, I.S.; "Immobilized Boronates for the Isolation and Separation of Bioanalytes"; *Biochromatography;* vol. 4, pp. 124–130; 1989.
Bergold, A. & Scouten, W.H.; "Borate Chromatography"; *Solid Phase Biochemistry;* Ch. 4, pp. 149–187; 1983 (USA).

Lorand, J.P. & Edwards, J.O.; "Polyol Complexes and Structure of the Benzeneboronate Ion"; *J. Org. Chem.;* vol. 24, p. 769; 1959 (USA).
Bowie, R.A. & Musgrave, O.C.; "Organoboron Compounds. Part V.* The Hydrolysis of Cyclic Phenylboronates"; *J. Amer. Chem. Soc.;* pp. 3945–3949; 1963 (USA).
Sienkiewicz, P.A. & Roberts, D.C.; "pH Dependence of Boronic Acid–Diol Affinity in Aqueous Solution"; *J. Inorg. Nucl. Chem.;* vol. 42, pp. 1559–1571; 1980 (USA).
Tanner, D.W. & Bruice, T.C.; "Boric Acid Esters" *J. Amer. Chem. Soc.;* vol. 89, pp. 6954–6971; 1967 (USA).
Kliegel, W. & Nanninga, D.; "Borchelate von Salicylaldoxim und Derivaten"; *Monatshefte Fur Chemie;* vol. 114; pp. 465–484; 1983 (FRG).

(List continued on next page.)

Primary Examiner—Richard L. Raymond
Attorney, Agent, or Firm—Blakely, Sokoloff, Taylor & Zafman

[57] ABSTRACT

The present invention relates to a novel class of phenylboronic acid complexing reagents useful for the preparation of bioconjugates, and the method of making and using such reagents. In the present invention, in the place of prior art Avidin-Biotin and Digoxigenin-anti-Digoxigenin systems, phenylboronic acid complexing reagents are utilized in conjunction with phenylboronic acid reagents (many of which are known in the prior art) to facilitate chemical conjugation without the use of intermediary biological macromolecules. Reagents suitable for the modification of a bioactive species for the purpose of incorporating a phenylboronic acid complexing moiety for subsequent conjugation to a different bioactive species having pendant phenylboronic acid moieties are of General Formula I or General Formula II.

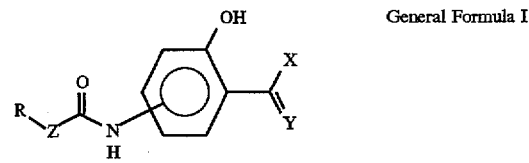

General Formula I

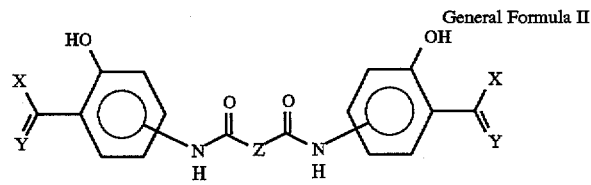

General Formula II wherein group X is selected from either H, OH, NH₂, NHCH₃, NHOH and NHOCH₃, wherein group Y is selected from either O, S and NH, and wherein group Z comprises a spacer which either separates the boronic acid complexing moiety from group R, as in General Formula I, or separates two boronic acid complexing moieties, as in General Formula II. Group R is a reactive electrophilic or nucleophilic moiety suitable for reaction of the phenylboronic acid complexing reagent with a bioactive species.

4 Claims, 6 Drawing Sheets

OTHER PUBLICATIONS

Imagawa et al.; "Characteristics and Evaluation of Antibody–Horseradish Perioxidase Conjugates, etc. "; *J. Applied Biochemistry;* vol. 4, pp. 41–57; 1982 (USA).

Kessler, C.; *Advances in Mutagenesis Research* (Obe, G. ed.); pp. 105–152; Springer–Verlag, Berlin/Heidelberg; 1990 (USA).

Brinkley, M.; "A Brief Survey of Methods for Preparing Protein Conjugates with Dyes, Haptens, and Cross Linking Reagents"; *Bioconjugate Chem.;* vol. 3, pp. 2–13; 1992 (USA).

Linder et al.; "Technetium Labeling of MonocLonal Antibodies with Functionalized BATOs 1. TcCL(DMG)$_3$PITC"; *Bioconjugate Chem.;* vol. 2, pp. 160–170; 1991 (USA).

Linder et al.; "Technetium Labeling of Monoclonal Antibodies with Functionalized BATOs 2. TcCl(DMG)$_3$CPITC Labeling of B72.3, etc." *Bioconjugate Chem.;* vol. 2, pp. 407–415; 1991 (USA).

Burnett et al.; "Synthesis of a Fluorscent Boronic Acid Which Reversibuluy Binds to Cell Walls, etc."; *Biochem. Biophys. Research Commun.;* vol. 96, pp. 157–162; 1980 (USA).

Steinberg, G.M. & Swidler, R.; "The Benzohydroxamate Anion";*J. Org. Chem. Vol.* ; vol. 30, pp. 2362–2365; 1965 (USA).

Bauer, L. & Exner, O.; "The Chemistry of Hydroxamic Acids and N–Hydroxyimides"; *Angew. Chem. Internat. Edit.;* vol. 13, pp. 376–384; 1974 (USA).

Cai, S.X. & Kean, J.; "o–Acetomidophenylboronate Esters Stabilized Toward Hydrolysis by an Intramolecular O–B Interation, etc."; *Bioconjugate Chem.;* vol. 2, pp. 317–322; 1991 (USA).

Ramalingam, K. & Nowotnik, D.; "Syntheses of Some Isothiocyanatophenylboronic Acids"; *Org. Prep. Proc. Int.;* vol. 23, 729–734; 1991 (USA).

Kliegel, W. & Nanninga, D.; "Borchelate Von Salicyladehydnitronen"; *Journal of Organometallic Chem.;* vol. 243, pp. 373–385; 1983 (USA).

Ripan et al.; "Etude Du Systeme Acide Borique–Salicylaldoxime en Solutions Aqueuses"; *Revue Roumaine de Chimie;* vol. 10, pp. 965–971; 1965 (FRA).

Roberts et al.; "Pluripotential Amino Acids"; *Tetrahedron Letters;* vol. 21, pp. 3435–3438; 1980 (USA).

Kemp, D.S. & Roberts, D.; "New Protective Groups for Peptide Synthesis—II The DOBZ Group, etc."; *Tetrahedron Letters;* vol. 52, pp. 4629–4632; 1975 (USA).

Kliegel, W. & Nanninga, D.; "Borchelate von N–substituierten Hydroxamsauren"; *Chem. Ber.;* vol. 116, pp. 2616–2629; 1983 (FRG).

Mikesova, M. & Bartusek, M.; "Reaction of Boric Acid with Salicylic and Chromotropic Acids and with Their Derivatives"; *Chem. Zvesti;* vol. 32(4), pp. 472–477; 1978.

Feeney, R.E., "Chemical Modification of Proteins: Comments and Perspectives"; *Int. J. Peptide Protein Res.;* vol. 29, pp. 145–161 (USA), 1987.

Means, G.E. & Feeney, R.E.; "Chemical Modifications of Proteins: History and Applications"; *Bioconjugate Chem.;* vol. 1, pp. 2–12 (USA), 1990.

O'Shannessy, D.J. & Quarles, R.H.; "Labeling of the Oligosaccharide Moieties of Immunoglobulins"; *J. Immunological Methods;*vol. 99, pp. 153–161 (1987) (USA).

van't Reit, B., Wampler, G.L., & Elford, H.L.; "Synthesis of Hydroxy–and Amino–Substituted Benzohydroxamic Acids, etc."; *J. Medicinal Chem.;* vol. 22, No. 5, 589–592, 1979 (USA).

Soundararajan, et al.; "Boronic Acids for Affinity Chromatography: Spectral Methods for Determination, etc."; *Analytical Biochem.;* vol. 178, pp. 125–134, 1989 (USA).

Goodchild, J.; "Conjugates of Oligonucleotides and Modified Oligonucleotides: A Review of Their Synthesis and Properties"; *Bioconjugate Chem.;* vol. 1, No. 3, pp. 165–193, 1990 (USA).

Kessler, C.; *Nonradioactive Labeling and Detection of Biomolecules;* Ch. 1–3, 1992 (USA).

Mearse, C.F., "Editorial: Introduction to Bioconjugate Chemistry"; *Bioconjugate Chem.;* vol. 1, No. 1, 1990 (USA).

Waggoner, A.S.; "Fluorescent Probes for Cytometry"; *Flow Cytometry and Sorting;* 2nd ed; pp. 209–225; 1990 (USA).

Borrebaeck, C.; "Strategy for the production of human monoclonal antibodies using in vitro activated B cells"; *J. Immun. Methods;* vol. 123; 157–165; 1989 (USA).

Chen, et al.; "Structure–Activity Relationships in a Series of 5–[(2,5–Dihydroxybenzyl) amino]salicylate, etc."; Chemical Abstracts; vol. 120; 322877v; 1994 (USA).

Hirano, et al.; "Silver halide color photographic material"; Chemical Abstracts; vol. 116; 140012u; 1992(USA).

Kawasaki, et al.; "Silver halide photographic material with improved storage stability"; Chemical Abstracts; vol. 109; 160505r; 1988 (USA).

Priewe, H.; et al.; "o–Hydroxybenzohydroxamic Acids"; Chemical Abstracts; vol. 52; 10184; 1958 (USA).

PHENYLBORONIC ACID COMPLEXING REAGENTS DERIVED FROM AMINOLALICYLIC ACID

This is a divisional of application Ser. No. 08/188,531, filed Jan. 28, 1994 now U.S. Pat. No. 5,594,151.

FIELD OF THE INVENTION

The present invention relates to the field of bioconjugate preparation, and more particularly, to a class of phenylboronic acid complexing reagents useful for the conjugation of biological macromolecules, and the method of making and using such reagents.

BACKGROUND OF THE INVENTION

Bioconjugation is a descriptive term for the joining of two or more different molecular species by chemical or biological means, in which at least one of the molecular species is a biological macromolecule. This includes, but is not limited to, conjugation of proteins, peptides, polysaccharides, hormones, nucleic acids, liposomes and cells, with each other or with any other molecular species that add useful properties, including, but not limited to, drugs, radionuclides, toxins, haptens, inhibitors, fluorophores, ligands, etc. Immobilization of biological macromolecules is also considered a special case of bioconjugation in which the macromolecule is conjugated, either reversibly or irreversibly, to an insoluble support. Bioconjugation is utilized extensively in biochemical, immunochemical and molecular biological research. Major applications of bioconjugation include; detection of gene probes, enzyme-linked immuno solid-phase assay, monoclonal antibody drug targeting and medical imaging.

AVIDIN-BIOTIN SYSTEM

Although numerous methods of bioconjugate preparation have been described, a significant number of those reported in the literature have been prepared by exploiting the Avidin-Biotin system, in which, the binding specificity of the protein Avidin (purified from egg white), or Streptavidin (purified from the bacterium Streptomyces avidinii), toward the cofactor Biotin (vitamin H) is utilized to bridge an Avidin conjugated macromolecule with a biotinylated macromolecule. Both Avidin and Streptavidin possess four Biotin binding sites of very high affinity ($K=10^{15}$ $mol^{-1}$). This system has been utilized extensively for enzyme-linked immuno solid-phase assay (ELISA), in which an enzyme-Avidin conjugate (useful for detection by reaction with the enzyme's substrate to afford a colored or chemiluminescent product) is employed to detect the presence of a biotinylated antibody, after first binding the antibody to an immobilized antigen or hapten. Applications of the Avidin-Biotin system number in the hundreds, and have recently been reviewed (Wilchek, M. and Bayer, E. A., *Methods in Enzymology*, 184 (1990)). Although utilized extensively, several limitations are known to be associated with the Avidin-Biotin system, which include nonspecific binding generally attributed to the basicity of the Avidin molecule, nonspecific binding attributed to the presence of carbohydrate residues on the Avidin molecule, and background interference associated with the presence of endogenous Biotin, which is ubiquitous in both eukaryotic and prokaryotic cells.

DIGOXIGENIN ANTI-DIGOXIGENIN SYSTEM

An alternative bioconjugation system designed to overcome the limitations associated with the Avidin-Biotin system has recently been developed for the detection of gene probes by ELISA (Kessler, C., Höltke, H.-J., Seibl, R., Burg, J. and Mühlegger, K., *Biol. Chem. Hoppe-Seyler*, 371, 917–965 (1990)). This system involves the use of the steroid hapten Digoxigenin, an alkaloid occuring exclusively in Digitalis plants, and Fab fragments derived from polyclonal sheep antibodies against Digoxigenin (anti-Digoxigenin). The high specificity of the various anti-Digoxigenin antibodies affords low backgrounds and eliminates the nonspecific binding observed in Avidin-Biotin systems. Digoxigenin-labeled DNA and RNA probes can detect single-copy sequences in human genomic Southern blots. The development of the Digoxigenin anti-Digoxigenin system has recently been reviewed (Kessler, C. (1990) in Advances in Mutagenesis Research (Obe, G. ed.) pp. 105–152, Springer-Verlag, Berlin/Heidelberg).

IMMOBILIZED BORONATES

Phenylboronic acids are known to interact with a wide range of polar molecules having certain requisite functionalities. Complexes of varying stability, involving 1,2-diols, 1,3-diols, 1,2-hydroxy acids, 1,3-hydroxy acids, 1,2-hydroxylamines, 1,3-hydroxylamines, 1,2-diketones and 1,3-diketones, are known to form with either neutral phenylboronic acid or phenylboronate anion. Consequently, immobilized phenylboronic acids have been exploited as chromatographic supports to selectively retain, from diverse biological samples, those molecular species having the requisite functionalities. Many important biological molecules including carbohydrates, catecholamines, prostaglandins, ribonucleosides, and steroids contain the requisite functionalities, and have been either analyzed or purified in this manner. The use of phenylboronic acid chromatographic media for the isolation and separation of biological molecules has been discussed in the following reviews (Singhal, R. P. and DeSilva, S. S. M. (1989) *Adv. Chromatog.*, 4, 124–130; Mazzeo, J. R. and Krull, I. S. (1989) *BioChromatog.*, 4, 124–130; and Bergold, A. and Scouten, W. H. (1983) in Solid Phase Biochemistry (Scouten, W. H. ed.) pp. 149–187, John Wiley & Sons, New York).

Phenylboronic acid, like boric acid, is a Lewis acid, and ionizes not by direct deprotonation, but by hydration to give the tetrahedral phenylboronate anion ($pK_\alpha=8.86$). Phenylboronic acid is three times as strong an acid as bode acid. Ionization of phenylboronic acid is an important factor in complex formation, in that, upon ionization, boron changes from trigonal coordination (having average bond angles of 120° and average bond lengths of 1.37 Å) to the tetrahedrally coordinated anion (having average bond angles of 109° and average bond lengths of 1.48 Å).

Molecular species having cis or coaxial 1,2-diol and 1,3-diol functionalities, and particularly carbohydrates, are known to complex with immobilized phenylboronate anion, to form cyclic esters under alkaline aqueous conditions (Lorand, J. P. and Edwards, J. O. (1959) *J. Org. Chem.* 24, 769).

Acidification of 1,2-diol and 1,3-diol complexs is know to release the diol containing species, presumably due to hydrolysis of the cyclic ester, which is induced by ring-strain associated with a five-membered cyclic boronic acid ester involving trigonal coordinated boron. Coplaner aromatic 1,3-diols, like 1,8-dihydroxynaphthalene, are known to complex even under acidic conditions due to the hydrolytic stability of six-membered cyclic boronic acid esters (Sienkiewicz, P. A. and Roberts, D. C. (1980) *J. Inorg. Nucl. Chem.*, 42, 1559–1571).

Molecular species having pendant 1,2-hydroxylamine, 1,3-hydroxylamine, 1,2-hydroxyamide, 1,3-hydroxyamide, 1,2-hydroxyoxime and 1,3-hydroxyoxime functionalities are also known to reversibly complex with phenylboronic acid, in a pH dependent manner, under alkaline aqueous conditions similar to those associated with the retention of diol containing species (Tanner, D. W. and Bruice, T. C. (1967) *J. Amer. Chem. Soc.*, 89, 6954).

Although immobilized phenylboronates have been utilized for chromatographic separation of biological molecules having the requisite functionalities, notwithstanding the substantial amount of research into bioconjugation, and the substantial amount of investment in this field, the selectivity of phenylboronic acid has not heretofore been exploited to enable the conjugation of biological macromolecules with one another or with other molecular species that add useful properties.

SUMMARY OF THE INVENTION

The present invention relates to a novel class of phenylboronic acid complexing reagents useful for the preparation of bioconjugates, and the method of making and using such reagents. In the present invention, in the place of prior an Avidin-Biotin and Digoxigenin-anti-Digoxigenin systems, phenylboronic acid complexing reagents are utilized in conjunction with phenylboronic acid reagents (many of which are known in the prior art) to facilitate chemical conjugation without the use of intermediary biological macromolecules. Bioconjugate preparation often involves the conjugation of several components including, but not limited to, proteins, peptides, polysaccharides, hormones, nucleic acids, liposomes and cells, with each other or with any other molecular species that add useful properties, including, but not limited to, drugs, radionuclides, toxins, haptens, inhibitors, fluorophores, ligands, and solid-phase supports. These various components utilized in bioconjugate preparation will collectively be termed bioactive species (BAS).

Reagents suitable for the modification of a bioactive species for the purpose of incorporating a phenylboronic acid complexing moiety for subsequent conjugation to a different bioactive species having pendant phenylboronic acid moieties are of General Formula I. Structurally related reagents suitable for conjugation of a bioactive species having pendant phenylboronic acid moieties are of General Formula II.

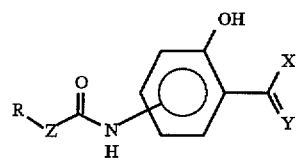

General Formula I

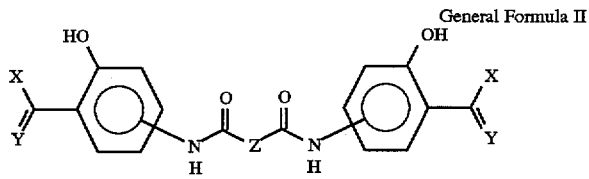

General Formula II wherein group X is selected from either H, OH, $NH_2$, $NHCH_3$, NHOH and $NHOCH_3$, wherein group Y is selected from either O, S and NH, and wherein group Z comprises a spacer which either separates the boronic acid complexing moiety from group R, as in General Formula I, or separates two boronic acid complexing moieties, as in General Formula II. Group R is a reactive electrophilic or nucleophilic moiety suitable for reaction of the phenylboronic acid complexing reagent with a bioactive species.

Reagents of General Formulas I and II are preferably those wherein group X is selected from either OH, NHOH and $NHOCH_3$, and group Y is O. Group Z is preferably selected from either an alkyl chain or polyethyleneglycol chain, of from 1 to 16 carbon equivalents in length, and which may contain intermediate amide functionalities, and is preferably $(CH_2)_n$, wherein n=1 to 5, or $(CH_2CH_2O)_n$, wherein n=2 to 4. Group Z may contain a cleavable disulfide bond.

Reagents of General Formula I are preferably those wherein group R is selected from, but is not limited to, amino, hydrazide, N-hydroxysuccinimidyl ester, N-hydroxysulfosuccinimidyl ester, isothiocyanate, bromoacetamide, iodoacetamide, maleimide and thiol moieties.

Reaction of a reagent of General Formula I with a bioactive species affords a semi-conjugate having pendant phenylboronic acid complexing moieties (one or more) of General Formula III, wherein the symbol labeled BAS represents the bioactive species, and groups X, Y and Z are as were previously defined.

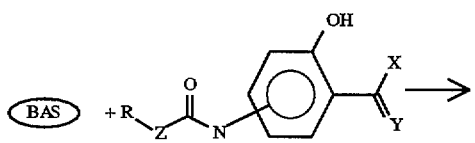

General Formula I

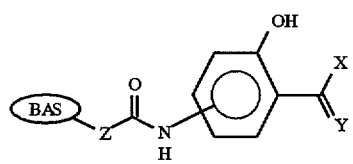

General Formula III

Similarly, phenylboronic acid reagents, described in greater detail in my copending application "PHENYLBO- RONIC ACID COMPLEXES FOR BIOCONJUGATE PREPARATION", Ser. No. 08/188,958, now U.S. Pat. No. 5,594,111 which is incorporated herein by reference, may be appended to a bioactive species to afford a semiconjugate having pendant phenylboronic acid moieties (one or more) of General Formula IV, wherein the symbol labeled BAS* represents a second bioactive species, differing from the bioactive species labeled BAS. Semiconjugates of General Formula IV involve either the tetrahedral phenylboronate anion under alkaline conditions, or triganol phenylboronic acid under neutral or acidic conditions.

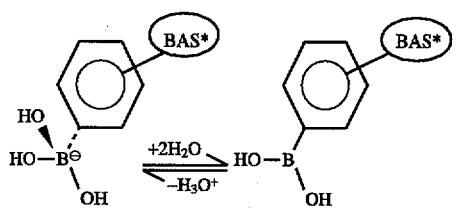

General Formula IV

A semiconjugate of General Formula III, prepared from bioactive species BAS and having pendent phenylboronic acid complexing moieties, may be complexed with a semiconjugate of General Formula IV, prepared from a second bioactive species BAS* and having pendant phenylboronic acid moieties, to afford a bioconjugate of General Formula V, wherein the symbols labeled BAS and BAS*, and groups X, Y and Z are as were previously defined. In this manner, biological macromolecules may be conjugated to one another or with other functionalities which impart useful properties.

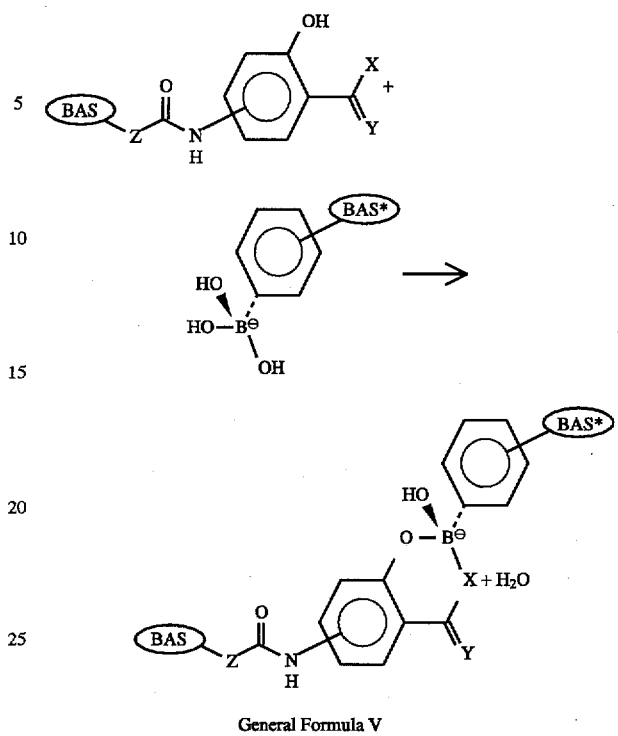

General Formula V

Similarly, a reagent of General Formula II may be complexed with a semiconjugate of General Formula IV, prepared from a bioactive species BAS*, to afford a bioconjugate of General Formula VI, wherein the symbol labeled BAS*, and groups X, Y and Z are as were previously defined. In this manner, two or more identical bioactive species BAS*, may be conjugated to one another. This process may be exploited to prepare enzyme aggregates, which are useful for high sensitivity detection during ELISA.

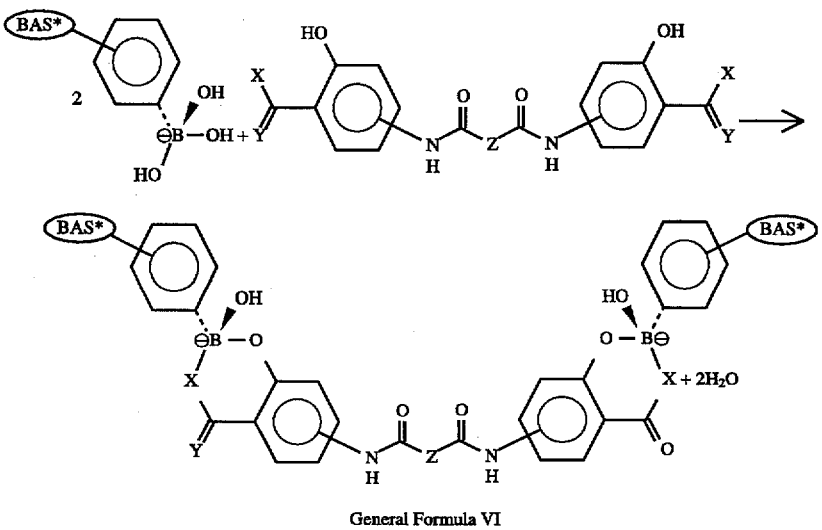

General Formula VI

Alternatively, a reagent of General Formula II may be complexed with a semiconjugate of General Formula IV, prepared from a bioactive species BAS, and a second semiconjugate of General Formula IV, prepared from a bioactive species BAS*, to afford a bioconjugate of General Formula VII, wherein the symbols labeled BAS and BAS*, and groups X, Y and Z are as were previously defined. In this manner, two or more differing bioactive species BAS and BAS*, may be conjugated to one another.

CH=CHCOOH, $CH_2CH_2COCH_3$, $CH_2CH_2Br$, $CH_2CH_2SSC_5H_4N$, and $CH_2CH_2COOH$, and the further functionalization of these compounds to other useful complexing reagents.

FIG. 2 illustrates an alternate synthesis of reagents of General Formula I, wherein group X is $NHOCH_3$, and wherein group Y is O.

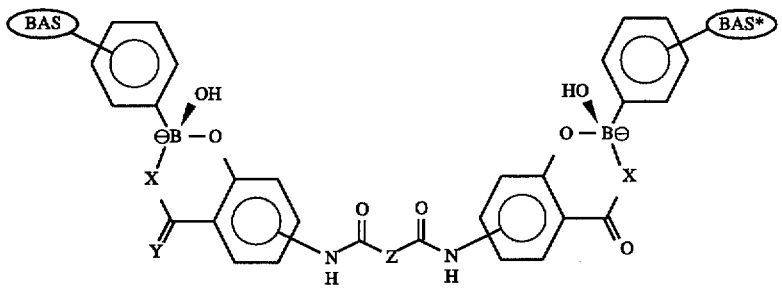

General Formula VII

Bioconjugates of General Formulas V, VI and VII may be prepared in buffered aqueous or aqueous/organic solutions. The bioconjugate is formed within a few minutes at room temperature. The stability of the bioconjugate at a given pH is determined by substituent groups X and Y. Bioconjugates of General Formulas V, VI and VII, wherein both groups X and Y are O, are stable in acidic aqueous solutions of approximate pH less than 4.5. Bioconjugates of General Formulas V, VI and VII, wherein group X is selected from either NH and $NCH_3$, and wherein group Y is selected from either O and S, are stable in buffered alkaline aqueous solutions over the approximate pH range 8.5 to 11.5. Similarly, bioconjugates of General Formulas V, VI and VII, wherein both groups X and Y are NH, are stable in buffered alkaline aqueous solutions over the approximate pH range 8.5 to 11.5. Bioconjugates of General Formulas V, VI and VII, wherein group X is selected from either NOH and $NOCH_3$, and group Y is selected from either O and S, are stable in buffered aqueous solutions over the broad approximate pH range 2.5 to 11.5.

The bioconjugation reaction (phenylboronic acid complexation) is insensitive to significant variations in ionic strength, temperature, the presence of organic solvents, and the presence of chaotropic agents (protein denaturants), which are incompatible with prior art systems wherein the structure of a biological macromolecule must be maintained to preserve requisite binding properties. In most instances, the constraints governing the formation of bioconjugates, by the system herein described, are limited to those imposed by the conditions required to maintain viability of the bioactive species.

DETAILED DESCRIPTION

Synthesis of Phenylboronic Acid Complexing Reagents of General Formula I

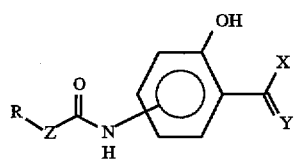

General Formula I

Reagents of General Formula I, wherein group X is selected from either $NH_2$, $NHCH_3$ and NHOH, and wherein group Y is O are derived from either 4-aminosalicylic acid or 5-aminosalicylic acid. As illustrated in FIG. I, 4- or 5-aminosalicylic acid is first esterified to afford either methyl 4-aminosalicylate or methyl 5-aminosalicylate, respectively. The ester is neutralized and then amidated by reaction with an amine selected from either ammonia, methylamine and hydroxylamine, to afford either a 4- or 5-aminosalicylamide of General Formula IX, wherein group X is selected from either $NH_2$, $NHCH_3$ and NHOH.

The compound of General Formula IX is next condensed with an activated carboxylic acid preferably selected from, but not limited to, succinic anhydride, methyl succinyl chloride, maleic anhydride, N-methoxycarbonylmaleimide, 3-bromopropionyl chloride, 3-iodopropionyl chloride, iodoacetyl chloride, bromoacetyl chloride and chloroacetyl chloride, to afford a compound of General Formula X, wherein group R is preferably selected from, but not limited to, either $CH_2CH_2COOH$, $CH_2CH_2COOCH_3$, $CH=CHCOOH$, $CH_2CH_2Br$, $CH_2CH_2I$, $CH_2I$, $CH_2Br$ and $CH_2Cl$, and wherein group X is as was previously defined.

Figure 1:
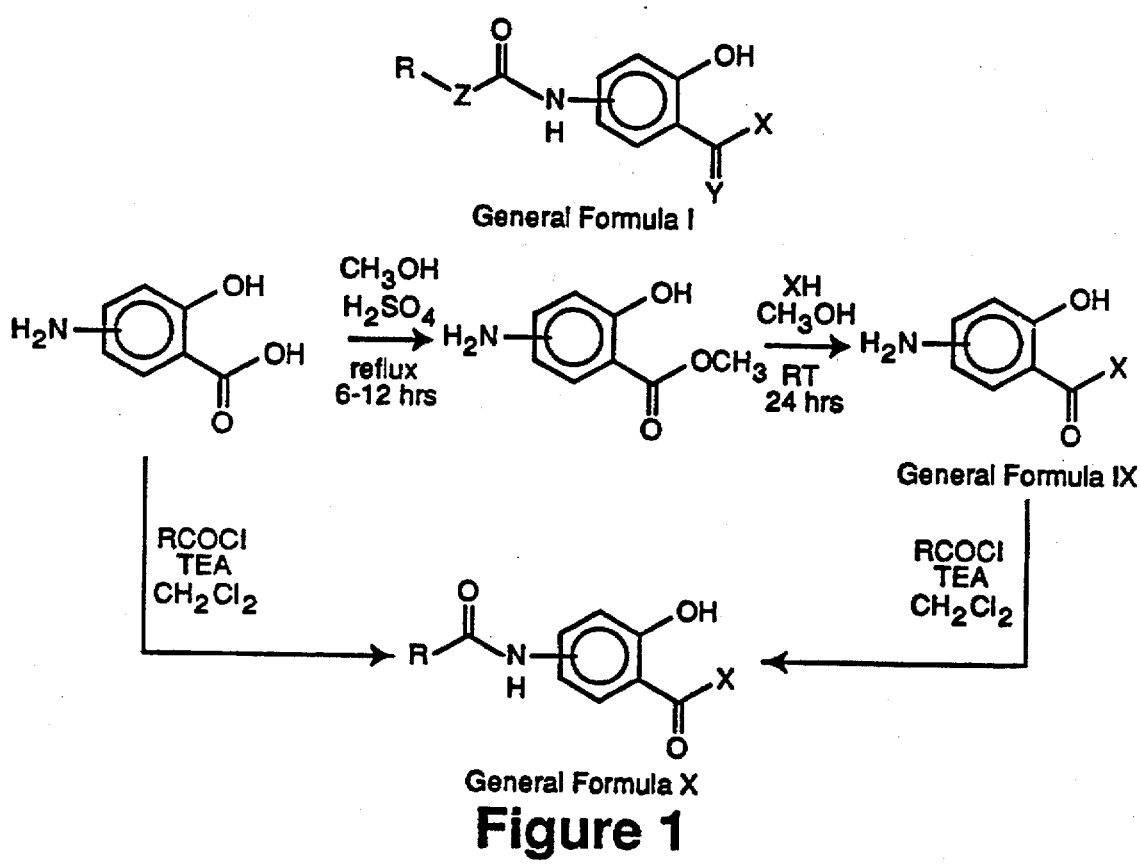
FIG. 1 illustrates the synthesis of reagents of General Formula I, wherein group X is selected from either OH, $NH_2$, $NHCH_3$ and NHOH, and wherein group Y is O.
Figure 1A:
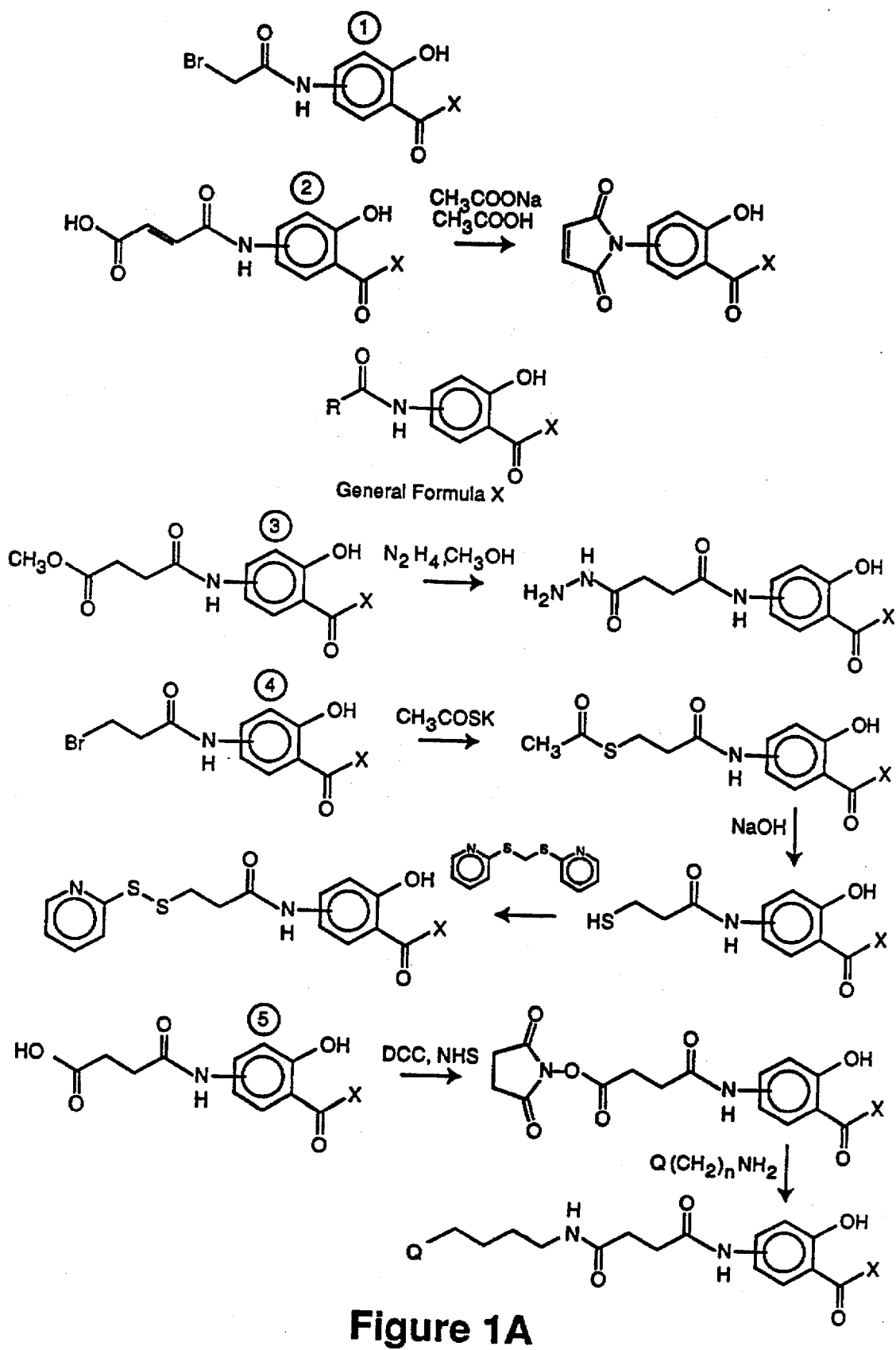
FIG. 1A illustrates compounds of general formula X wherein group R is selected from $CH_2I$, $CH_2Br$.

Compounds of General Formula X, wherein group R is selected from either $CH_2I$ and $CH_2Br$ (FIG. 1A, (1)), are useful as thiol reactive reagents suitable for appending a phenylboronic acid complexing moiety to a bioactive species having pendant thiol groups.

Compounds of General Formula X, wherein group X is OH, and wherein group R is $CH_2I$, have been prepared previously for use as enzyme inhibitors (Holbrook, J. J., Roberts, P. A. and Wallis, R. B. (1973) *Biochem. J.*, 133, 165–171).

Compounds of General Formula X, wherein group R is $CH=CHCOOH$ (FIG. 1A, (2)), may be further functionalized by ring closure to afford a thiol reactive maleimide reagent suitable for appending a phenylboroic acid complexing moiety to a bioactive species having pendant thiol groups.

Compounds of General Formula X, wherein group R is $CH_2CH_2COOCH_3$ (FIG. 1A, (3)), may be further functionalized by reaction with hydrazine hydrate to afford a hydrazide reagent of General Formula X, wherein R is $CH_2CH_2CONHNH_2$, suitable for appending a phenylboronic acid complexing moiety to a bioactive species having pendant aldehyde groups (which result from periodate oxidation of carbohydrate residues).

Compounds of General Formula X, wherein group R is selected from either $CH_2CH_2Br$ and $CH_2CH_2I$ (FIG. 1A, (4)), may be further functionalized by reaction with potassium thiolacetate to afford an intermediate which, upon deprotection, affords a thiol containing compound of General Formula X, wherein group R is $CH_2CH_2SH$. The thiol containing compound of may be activated by reaction with a reagent preferably selected from, but not limited to 2,2'-dithiodipyridine, 4,4'-dithiodipyridine and 2,2'-dithiodi(3-nitropyridine), to prepare an activated disulfide containing reagent suitable for appending a phenylboronic acid complexing moiety to a bioactive species having pendant thiol groups, through a cleavable disulfide bond.

Compounds of General Formula X, wherein group X is selected from either $NH_2$ and $NHCH_3$, and wherein group R is $CH_2CH_2COOH$ (FIG. 1A, (5)), may be further functionalized by reaction with dicyclohexylcarbodiimide (DCC) and a reagent preferably selected from, but not limited to, either N-hydroxysuccinimide (NHS) and N-hydroxysulfosuccinimide (SNHS), to afford an activated ester reagent suitable for appending a phenylboronic acid complexing moiety to a bioactive species having pendant amine groups.

Activated esters of General Formula X, wherein group X is selected from either $NH_2$ and $NHCH_3$, and wherein group R is $CH_2CH_2CO$—NHS, are useful synthetic intermediates for the preparation of reagents of General Formula I, wherein group Z is comprised of an alkyl chain or polyethyleneglycol chain, of greater than 6 carbon equivalents in length (as illustrated in FIG. 1A).

Compounds of General Formula X, wherein group X is NHOH, can not be routinely employed to prepare reagents having activated ester moieties, due to problems which arise when the carboxylic acid group is activated in the presence of both NHS and the benzohydroxamic acid group associated with the phenylboronic acid complexing moiety. This represents a limitation, due to the popularity of N-hydroxysuccinimide reagents, and the fact that only reagents of General Formula I, wherein group X is selected from either NHOH and $NHOCH_3$, form stable complexes of General Formulas V, VI and VII, over a broad pH range.

To overcome this limitation, an alternate synthetic route is employed to prepare activated ester reagents of General Formula I, wherein group X is $NHOCH_3$, and group Y is O (FIG. 2). 4-Aminosalicylic acid or 5-aminosalicylic acid is condensed with methyl succinyl chloride to afford a compound of General Formula X, wherein group X is OH, and wherein group R is $CH_2CH_2COOCH_3$. Subsequent reaction with N,N-carbonyldiimidazole (CDI) followed by addition of methoxylamine hydrochloride, affords a compound of General Formula XI, wherein group X is $NHOCH_3$. Alkaline hydrolysis of the carboxylic acid ester group affords a compound having a free carboxylic acid group. Subsequent activation of the carboxylic acid group by reaction with DCC and a reagent preferably selected from, but not limited to, either NHS and SNHS, affords an activated ester reagent of General Formula XII, wherein group X is $NHOCH_3$, suitable for appending a phenylboronic acid complexing moiety to a bioactive species having pendant amine groups.

N-Hydroxysuccinimidyl esters of General Formula XII, wherein group X is $NHOCH_3$, are useful synthetic intermediates for the preparation of reagents of General Formula I, wherein group Z is comprised of an alkyl chain or polyethyleneglycol chain, of greater than 6 carbon equivalents in length.

Figure 2:
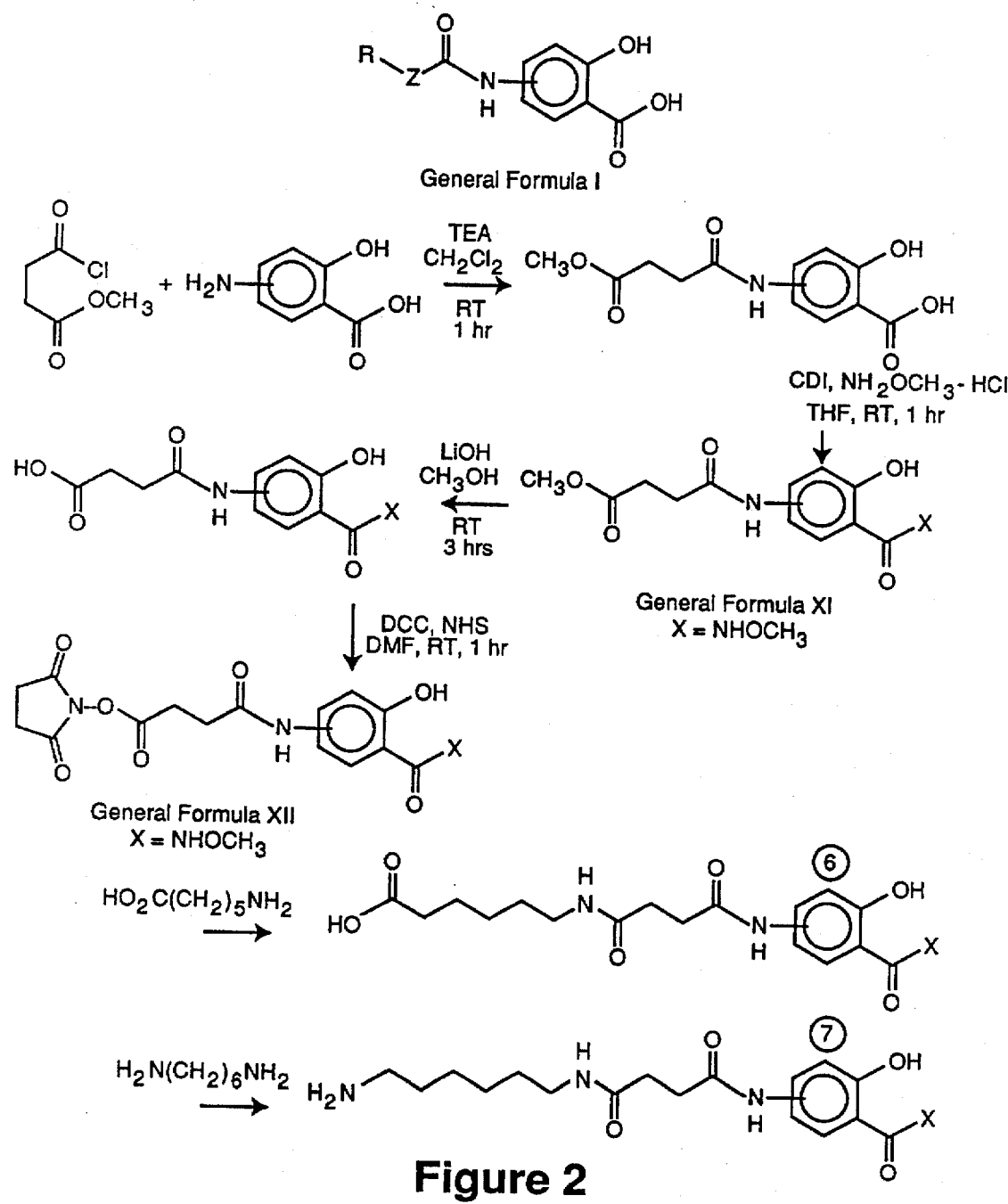

Compounds of General Formula XII, wherein group X is $NHOCH_3$, may be further functionalized by reaction with a reagent preferably selected from, but not limited to 6-aminohexanoic acid, 4-aminobutanoic acid, N-tert-butoxycarbonyl-1,6-diaminohexane (N-Boc-1,6-diaminohexane) and N-Boc-1,4-diaminobutane, to afford, after removal of the Boc protecting group, if required, a compound having an extended spacer and either a terminal carboxylic acid group (FIG. 2, (6)), or a terminal amine group (FIG. 2, (7)). The aforementioned reagents, having pendant carboxylic acid groups, are useful for the preparation SNHS ester, SNHS ester and hydrazide containing reagents having long spacers, which are useful to overcome steric hindrance know to be associated with biological macromolecules of high molecular weight. Similarly, the aforementioned reagents, having pendant amine groups, are useful for the preparation iodoacetamide, maleimide and activated disulfide containing compounds having long spacers. Additionally, the aforementioned reagents having either pendant carboxylic acid groups or pendant amine groups are useful synthetic intermediates for the preparation of solid-phase supports.

Synthesis of Phenylboronic Acid Complexing Reagents of General Formula II

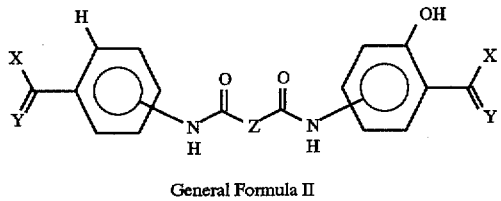

General Formula II

Reagents of General Formula II, wherein group X is selected from either $NH_2$, $NHCH_3$ and NHOH, and wherein group Y is O, are derived from either 4- or 5-aminosalicylic acid in a manner analogous to that employed to prepare reagents of General Formula I. A compound of General Formula IX, prepared as previously described, is condensed with an activated dicarboxylic acid preferably selected from, but not limited to, succinyl chloride, adipoyl chloride, adiptic acid diisobutylcarbonate, suberoyl chloride, 3,3'-dithiopropionyl chloride, 3,6,9-trioxaundecanedioyl chloride and 3,6,9-trioxaundecanedioic acid diisobutylcarbonate, to afford a compound of General Formula II, wherein group X is selected from either $NH_2$, $NHCH_3$ and NHOH, wherein group Y is O, and wherein group Z is selected from, but not limited to, either $(CH_2)_2$, $(CH_2)_4$, $(CH_2)_6$, $(CH_2)_2SS(CH_2)_2$ and $CH_2(OCH_2CH_2)_2OCH_2$, respectively.

Figure 3:
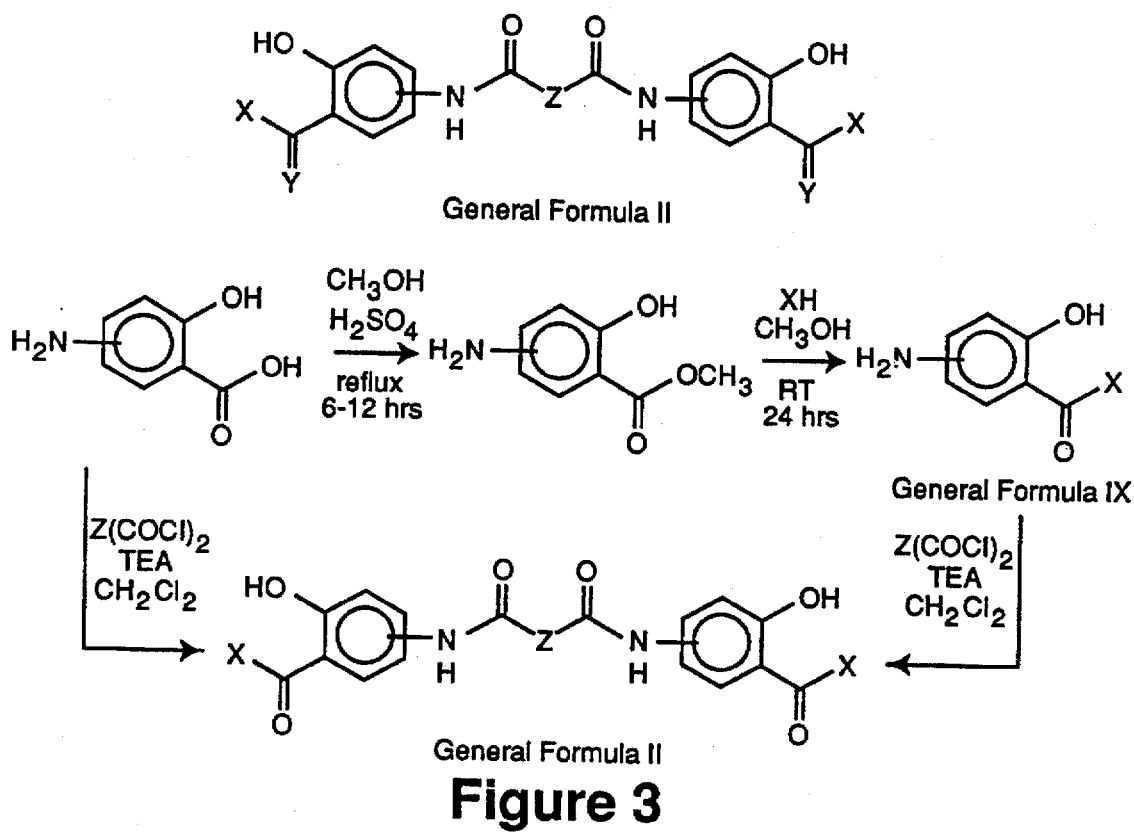
FIG. 3 illustrates the synthesis of reagents of General Formula II, wherein group X is selected from either OH, $NH_2$, $NHCH_3$ and NHOH, and wherein group Y is O.
Figure 3A:
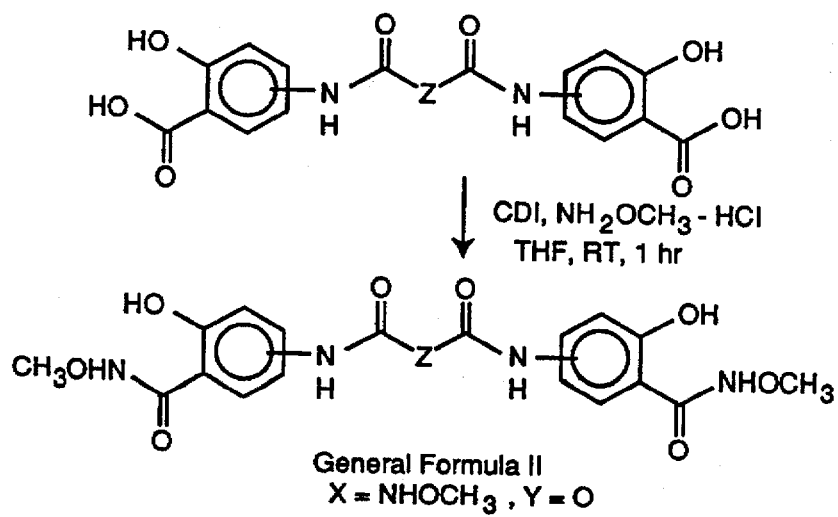
FIG. 3A illustrates the synthesis of reagents of general formula II, wherein group X is $NHOCH_3$, and wherein group Y is O.

Reagents of General Formula II, wherein group X is $NHOCH_3$, and wherein group Y is O, are prepared by an alternate synthetic route, in a manner analogous to the preparation of reagents of General Formula I, wherein group X is $NHOCH_3$. Either 4- or 5-aminosalicylic acid is condensed with an activated dicarboxylic acid preferably selected from, but not limited to, succinyl chloride, adipoyl chloride, adiptic acid diisobutylcarbonate, suberoyl chloride, 3,3'-dithiopropionyl chloride and 3,6,9-trioxaundecanedioyl chloride and 3,6,9-trioxaundecanedioic acid diisobutylcarbonate, to afford a compound of General Formula II, wherein group X is OH, wherein group Y is O, and wherein group Z is selected from, but not limited to, either $(CH_2)_2$, $(CH_2)_4$, $(CH_2)_6$, $(CH_2)_2SS(CH_2)_2$ and $CH_2(OCH_2CH_2)_2OCH_2$, respectively (FIG. 3A).

Subsequent reaction of a compound of General Formula II, wherein group X is OH, wherein group Y is O, and wherein group Z is selected from, but not limited to, either $(CH_2)_2$, $(CH_2)_4$, $(CH_2)_6$, $(CH_2)_2SS(CH_2)_2$ and $CH_2(OCH_2CH_2)_2OCH_2$, with CDI followed by addition of methoxylamine hydrochloride, affords a compound wherein group X is $NHOCH_3$, and wherein groups Y and Z are as were previously defined.

Bioconjugate Preparation

Figure 4:
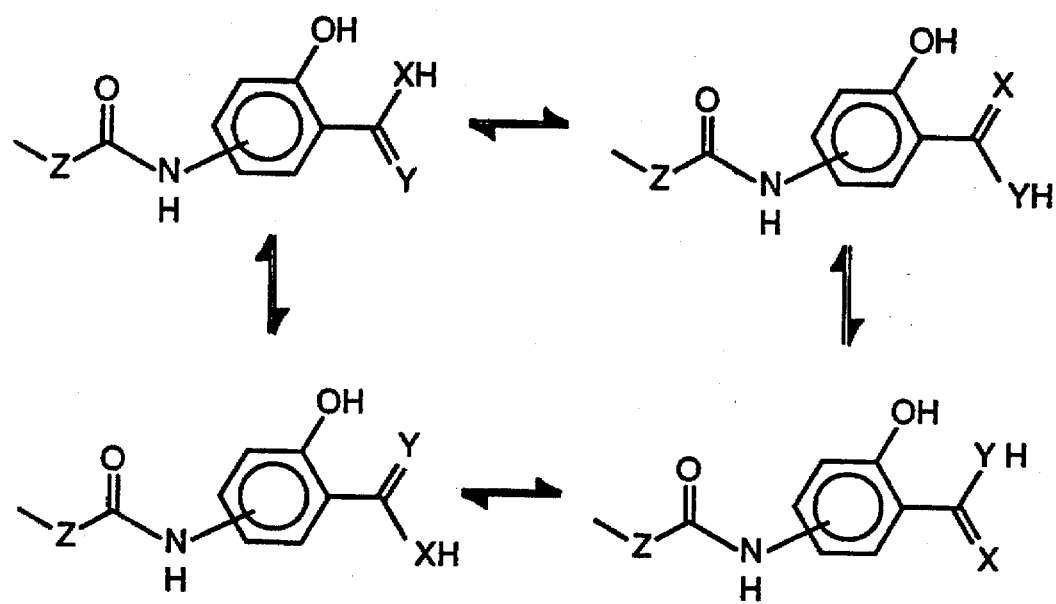
FIG. 4 illustrates tautomeric and conformational isomers of compounds of General Formula I and II which may contribute to phenylboronic acid complexation.
Figure 5:
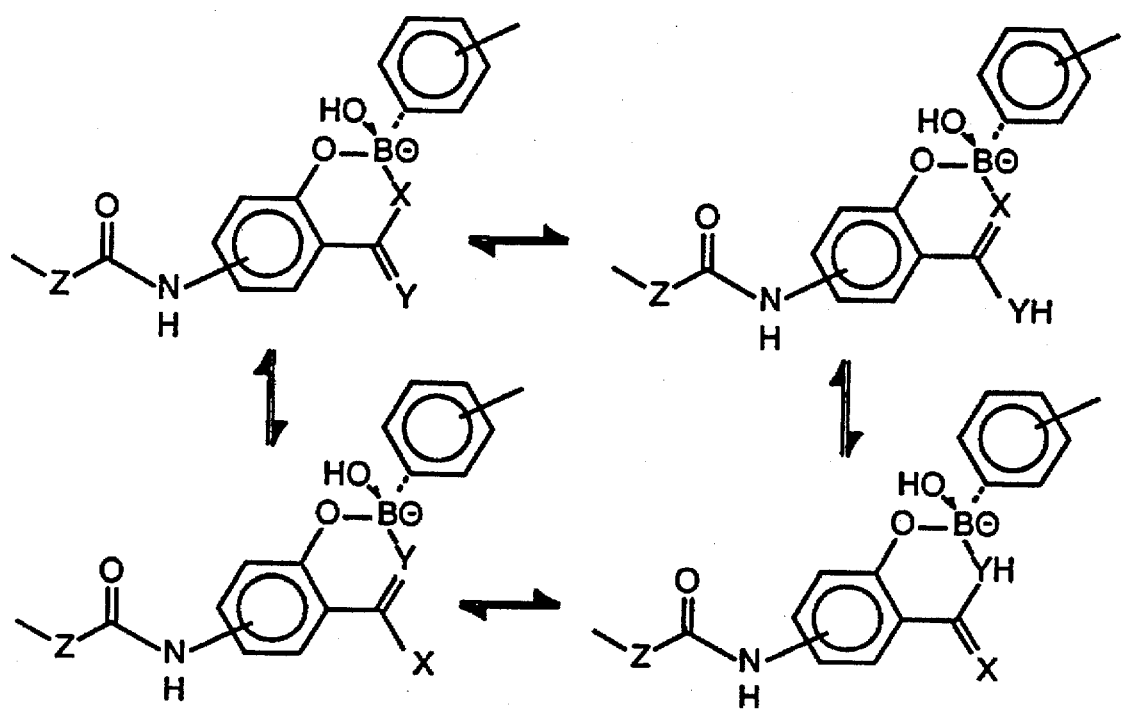
FIG. 5 illustrates tautomeric and conformational isomers of compounds of General Formula I and II shown complexed with phenylboronic acid.

Bioconjugates of General Formulas V, VI and VII may be prepared in buffered aqueous or aqueous/organic solutions. Preferred buffers include acetate, citrate, phosphate, carbonate and diglycine. Borate and Tris buffers should be avoided due to their ability to complex with the phenylboronic acid complexing moiety and phenylboronic acid moiety, respectively. The bioconjugate is formed within 1 to 15 minutes at room temperature. The reaction is insensitive to variations in ionic strength over the range 0.01 to 2 molar. Stability of the conjugate increases with increasing temperature, limited only by the volatility of the buffer. The addition of organic solvents including acetonitrile, methanol, ethanol, isopropanol, butanol, N,N-dimethylformamide and dimethylsulfoxide serves to further stabilize conjugates. Chaotropic reagents including urea, guanidine hydrochloride and formamide also serve to further stabilie conjugates. Once formed, bioconjugates are stable upon removal of water, and can be purified by lyophilization. The stability of the bioconjugate at a given pH is determined by substituent groups X and Y. For compounds of General Formulas I and II, individuals skilled in the art will recognize that a number of tautomeric and conformational isomers exist in equilibrium as illustrated in FIG. 4 (bioactive species omitted for clarity). Each of the isomers depicted in FIG. 4 may contribute to phenylboronic acid complexation as illustrated in FIG. 5 (bioactive species omitted for clarity). For all substituent groups X and Y, except when both X and Y are O, conjugates are stable in buffered alkaline aqueous solutions over the approximate pH range 8.5 to 11.5.

Figure 6:
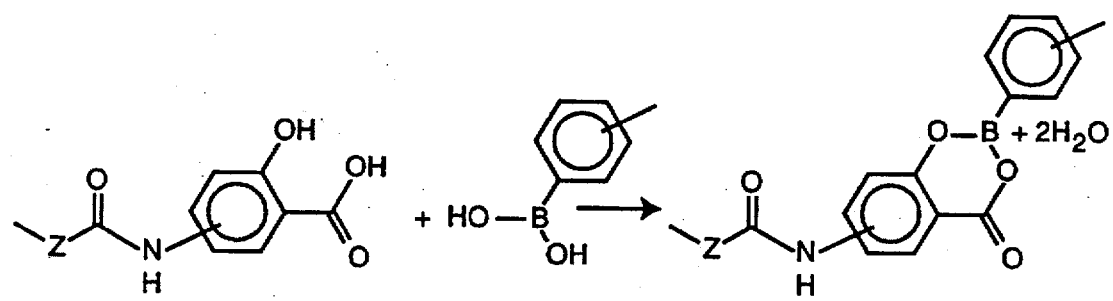
FIG. 6 illustrates the formation of complexes involving salicylic acid at low pH.

Phenylboronic acid complexes of General Formulas V, VI and VII, wherein both groups X and Y are O, represent a novel situation in which conjugates are stable in buffered acidic aqueous solutions of approximate pH less than 4.5. This range of pH stability results from the requirement that group X must posses an acidic hydrogen if a stable conjugate is to form. As illustrated in FIG. 6 (bioactive species omitted for clarity), conjugates will only form at low pH where the salicylic acid moiety is protonated.

Figure 7:
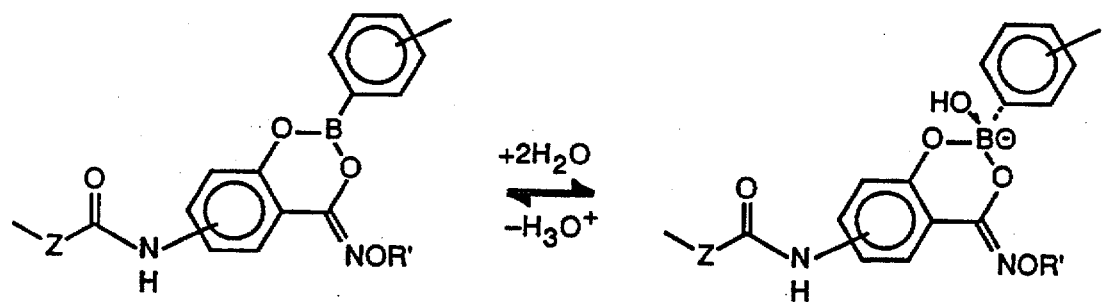
FIG. 7 illustrates the formation of complexes involving 2-hydroxybenzohydroxamic acid under both acidic and alkaline conditions.

Phenylboronic acid complexes of General Formulas V, VI and VII, wherein group X is selected from either NOH and $NOCH_3$, and wherein group Y is O, represent a novel situation in which bioconjugates are stable in buffered aqueous solutions over the approximate pH range 2.5 to 11.5. The wide range of pH stability is thought to result from the presence of a coplanar 1,3-diol complexing moiety associated with the enol form of 2-hydroxybenzohydroxamic acid. As illustrated in FIG. 7 (bioactive species omitted for clarity), the enol tautomer affords a stable complex with both neutral phenylboronic acid, under acidic conditions, and phenylboronate anion, under alkaline conditions, due to the stability of the six-membered cyclic ester (wherein R' is selected from either H and $CH_3$).

Example I

Preparation of 4-Amino-2-hydroxybenzohydroxamic Acid

Absolute methanol (100 mL) and fresh concentrated $H_2SO_4$ are carefully combined in a 250 mL round button flask with continuous stirring (exothermic). 4-Aminosalicylic acid (10.0 grams, 65.4 mmol) is added to produce a dark solution, which is heated under reflux for 6 hours. The product is allowed to cool and then concentrated on a rotary evaporator to approximately half the original volume. At this point a solid precipitate appears. The concentrate is poured into 400 mL of water, and the resulting suspension titrated to approximately pH 3, by stepwise addition of 5N NaOH (to pH 6.5), followed by solid $Na_2CO_3$, with evolution of $CO_2$ gas. The concentrate was chilled on ice, and the resulting precipitate collected by filtration. The filtrate is washed with cold water, and then dried in vacuo over NaOH pellets, to afford 9.6 grams (88% yield) of methyl 4-aminosalicylate, a pale lavendar powder (m.p. 115°–117° C.). The structure was confirmed by $^1H$ NMR spectrometry in d6-acetone.

NaOH (4.0 grams) in 16 mL of water is carefully added to hydroxylamine hydrochloride (2.8 grams, 40 mmol) and 20 grams of ice. After dissolution, $Na_2SO_3$ (0.4 grams) is added, followed by methyl 4-aminosalicylate (3.35 grams, 20 mmol). The resulting solution is stirred for up to 24 hours at room temperature, the course of the reaction is monitored every few hours by reverse phase HPLC. The resulting solution is chilled on ice and acidified by addition of 25% $H_2SO_4$. A precipitate is first formed at approx. pH 6. The pH is finally adjusted to approx. pH 4, and the pale tan precipitate collected by filtration. The product is dried in vacuo over $P_2O_5$, to afford 3.0 grams (89% yield) of 4-amino-2-hydroxybenzohydroxamic acid (m.p. 180°–181° C. The structure was confirmed by $^1H$ NMP, spectrometry in $d_6$-DMSO.

4-Amino-2-hydroxybenzohydroxamic acid is a key synthetic intermediate in the preparation of reagents of both General Formulas I and II, wherein group X is NHOH, and wherein group Y is O. Reagents having the 2-hydroxybenzohydroxamic acid moiety can form bioconjugates which are stable in buffered aqueous solutions over the approximate pH range 2.5 to 11.5.

Example II

Preparation of An Aldehyde Reactive Phenylboronic Acid Complexing Reagent of General Formula I To an ice-cooled, stirred solution of 4-Amino-2-hydroxybenzohydroxamic acid (8.4 grams, 0.05 mol), prepared as described above, in 150 mL of water containing $NaHCO_3$ (7.0 grams, 0.02 mol), 3-carbomethoxypropionyl chloride (9.0 grams, 0.06 mol) is added dropwise over 15 min. After stirring at 0°–5° C. for 1 hr., the solution is acidified with cold 6N HCl. The precipitate is collected and dried in vacuo over NaOH pellets, to afford 13.5 grams (96% yield) of crude N-4-(3-carbomethoxypropionamido)-2-hydroxy-benzohydroxamic acid, which is utilized without further purification.

To a solution of N-4-(3-carbomethoxypropionamido)-2-hydroxybenzohydroxamic acid (10 grams, 0.035 mol) in 50 mL of methanol is added hydrazine hydrate (12 mL). The reaction is allowed to proceed overnight at room temperature, and the product is filtered and washed with ether. The product is recrystallized twice from dimethylformamide to afford 7.3 grams (78% yield) of N-4-(3-hydrazidopropionamido)-2-hydroxybenzohydroxamic acid.

Example III

Application of An Aldehyde Reactive Phenylboronic Acid Complexing Reagent

Glycoproteins, and particularly antibodies, may be conjugated with an aldehyde reactive phenylboronic acid complexing hydrazide reagent after treatment of the protein with from 5 to 20 mM sodium meta periodate ($NaIO_4$), in from 0.1 to 0.5M sodium acetate buffer at pH 5 to 6, containing up to 0.2M sodium chloride, at 0° C., for from 30 minutes to 4 hours. The excess periodate is removed by dialysis or desalting, and the activated protein, having pendant adjacent aldehyde moieties resulting from periodate oxidation of carbohydrate residues having adjacent coaxial 1,2-diol moieties, is condensed with the hydrazide reagent, for from 1 to 24 hours at room temperature, to afford a semiconjugate having pendant phenylboronic acid complexing moieties covalently appended to the protein throught a Shiff base (an imine) type linkage. The stability of the linkage to the protein may be increased, if desired, by mild sodium cyanoborohydride reduction of the Schiff base to the corresponding alkylamine.

It is important to note that sodium meta periodate oxidation of a glycoprotein activates the protein toward reaction with a hydrazide type reagent while simultaneously removing most naturally occuring phenylboronic acid complexing sites (coaxial 1,2-diols) associated with glycoproteins.

Example IV

Preparation of A Thiol Reactive Phenylboronic Acid Complexing Reagent of General Formula I To an ice-cooled, stirred solution of 5-Aminosalicylamide (10.0 grams, 0.073 mol), in 300 mL of water containing $NaHCO_3$ (42.0 grams, 0.5 mol), iodoacetyl chloride (18.4 grams, 0.09 mol) is added dropwise over 15 min. After stirring at 0°–5° C. for 1 hr., the solution is acidified with cold 6N HCl. The precipitate is collected and dried in vacuo over NaOH pellets, to afford 21.3 grams (96% yield) of crude 5-(iodoacetamido)salicylamide.

Example V

Application of A Thiol Reactive Phenylboronic Acid Complexing Reagent

Proteins containing disulfide bonds (cystine residues) or cysteine residues may be modified with a thiol reactive phenylboronic acid complexing reagent, such as 5-(iodoacetamido)salicylamide. Disulfide bonds are first reduced, if required, by reaction with 2-mercaptoethanol or dithiothreitol, in alkaline aqueous solution which has been throughly degassed. The excess reducing reagent is removed by dialysis or desalting, and the protein reacted with the alkylating reagent in neutral aqueous solution, for 1 hour at 4° C., to afford a semiconjugate having pendant phenylboronic acid complexing moieties covalently appended to the protein. Upon completion of the reaction, the excess reagent is removed by desalting.

Example VI

Preparation of An Amine Reactive Phenylboronic Acid Complexing Reagent of General Formula I To an ice-cooled, stirred solution of 4-Aminosalicylic acid (7.7 grams, 0.05 mol), prepared as described above, in 150 mL of water containing NaHCO₃ (7.0 grams, 0.02 mol), 3-carbomethoxypropionyl chloride (9.0 grams, 0.06 mol) is added dropwise over 15 min. After stirring at 0°–5° C. for 1 hr., the solution is acidified with cold 6N HCl. The precipitate is collected and dried in vacuo over NaOH pellets, to afford 11.9 grams (89% yield) of crude N-4-(3-carbomethoxypropionamido)salicylic acid, which is utilized without further purification.

To a vigorously stirred solution of N-4-(3-carbomethoxypropionamido)salicylic acid (10.0 grams, 0.036 mol) in 50 mL of tetrahydrofuran is added stepwise 1,1'-carbonyldiimidazole (5.84 grams, 0.036 mol) and methoxylamine hydrochloride (3.0 grams, 0.036 mol). The vessel is fitted with a drying tube and the reaction vigorously stirred for 30 min. at room temperature. Imidazolium hydrochloride, which separated during the course of the reaction, is removed by filtration. The filtrate is concentrated on a rotary evaporator to afford an amber oil, which is dissolved in 10 mL of warm tetrahydrofuran, and then added to 150 mL of 2N H₂SO₄. The precipitate is collected by filtration, washed with 2N H₂SO₄, washed with water, and then dried overnight in vacuo over NaOH pellets to afford 10.0 grams (94% yield) of N-4-(3-carbomethoxypropionamido)-2-hydroxy-O-methylbenzohydroxamic acid.

N-4-(3-Carbomethoxypropionamido)-2-hydroxy-O-methylbenzohydroxamic acid (7.4 grams, 0.025 mol) is dissolved in 25 mL of 0.2N methanolic LiOH. The solution is stirred overnight at room temperature under nitrogen. Methanol is removed on a rotary evaporator, and the residue dissolved 150 mL of water. Acidifation of the solution to approximately pH 2 with 2N H₂SO₄ is followed by extraction into 100 mL of ether. A second extration into ether is followed by drying of the combined ether extracts over anhydrous Na₂SO₄. The product is concentrated on a rotary evaporator and then dried overnight in vacuo over P₂O₅, to afford 6.28 grams (89% yield) of N-4-succinamido-2-hydroxy-O-methylbenzohydroxamic acid.

N-4-succinamido-2-hydroxy-O-methylbenzohydroxamic acid (5.65 grams, 0.02 mol) is dissolved in 50 mL of hot dimethylformamide and allowed to cool to room temperature. To the stirred solution is added N-hydroxysuccinimide (2.3 grams, 0.02 mol) followed by a freshly prepared solution of dicyclohexylcarbodiimide (4.1 grams, 0.02 mol) in 10 mL of dimethylformamide. The resulting suspension is stirred overnight at room temperature. Dicyclohexylurea is filtered from solution, and the filtrate concentrated on a rotary evaporator to a minimum volume. The residue is precipitated with ether, and the precipitate collected by filtration, washed with ether, washed with 2-propanol, and then dried briefly in vacuo over P₂O₅, to afford 5.6 grams (74% yield) of N-4-succinamido-2-hydroxy-O-methlybenzohydroxamic acid succinimidyl ester. The product is stored in a freezer at −15° C.

Example VII

Application of An Amine Reactive Phenylboronic Acid Complexing Reagent

Proteins may be conjugated with amine reactive phenylboronic acid complexing reagents by reaction with the side-chain ε-amino groups of lysine residues, to afford a semiconjugate having pendant phenylboronic acid complexing moieties covalently appended to the protein through stable amide bonds. Mildly alkaline aqueous buffers, in the pH range 7.8 to 8.8, should be employed so as to insure that the amino group is unprotonated, while minimizing hydrolysis of the NHS ester. Primary amine containing buffers including Tris and glycine must be avoided, so as to avoid cross-reactivity. Solid-phase supports having pendant primary amine moieties may be functionalized, in an analogous manner, by reaction with phenylboronic acid complexing reagents to afford solid-phase supports having pendant phenylboronic acid complexing moieties.

Example VIII

Preparation of A Phenylboronic Acid Complexing Reagent of General Formula II

4-Amino-2-hydroxybenzohydroxamic acid (6.4 grams, 0.038 mol) is dissolved in 50 mL of dry dichloromethane. Triethylamine (5.3 mL, 0.038 mol) is added followed by the dropwise addition of a solution of 3,6,9-trioxaundecanedioyl chloride (5.0 grams, 0.019 mol) in 50 mL of dry dichloromethane, over a period of 2 hours. Triethylammonium hydrochloride is removed by filtration, and the filtrate washed with water (2×100 mL), saturated NaHCO₃ (2×100 mL), saturated NaCl (100 mL), and dried over anhydrous Na₂SO₄. The solvent is removed on a rotary evaporator and the residue recrystallized from methanol (100 mL) to afford 6.0 grams (61% yield) of colorless crystals. The structure was confirmed by ¹H NMR spectrometry in d₆-DMSO.

Example IX

Application of A Phenylboronic Acid Complexing Reagent of General Formula II

Proteins which have been conjugated to phenylboronic acid may be cross-linked by the action of reagents of General Formula II. This process is particularly useful for the preparation of protein aggregates, which are useful for modifying the properties of protein stability and solubility. Additionally, enzyme aggregates, prepared by cross-linking, are useful for amplifying the sensitivity or ELISA. This principle is exploited in the Avidin-Biotin system by the use of Avidin-Biotin complexes (called ABC complexes), in which a biotinylated enzyme is first employed to form a high molecular weight complex with Avidin (by cross-linking), prior to introduction of the complex into an ELISA for the high sensitivity detection of a biotinylated antibody.

I claim:

1. A semiconjugate having the General Formula III as follows

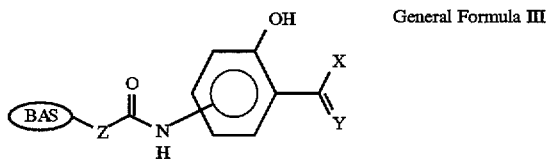

General Formula III wherein group X is selected from the group consisting of H, OH, NH₂, NHCH₃, NHOH and NHOCH₃, wherein group Y is selected from O, S and NH, wherein group Z is a spacer selected from the around consisting of an alkyl chain of from 1 to 16 carbon equivalents in length and a polyethylene glycol chain, up to 12 carbon equivalents in length, wherein said alkyl chain may contain intermediate amide functionalities and wherein said Z group may contain a cleavable disulfide bond, and wherein BAS is a biologically active species.

2. The semiconjugate of claim 1, wherein group X is NHOH and group Y is O.

3. The semiconjugate of claim 1, wherein group Z is selected from $(CH_2)_n$, wherein n=1 to 5, and $(CH_2CH_2O)_{n'}$, wherein n'=2 to 4.

4. The semiconjugate of claim 1, wherein group Z contains a cleavable disulfide bond.

* * * * *

UNITED STATES PATENT AND TRADEMARK OFFICE
CERTIFICATE OF CORRECTION

PATENT NO.   :   5,668,257
DATED        :   September 16, 1997
INVENTOR(S)  :   Mark L. Stolowitz It is certified that error appears in the above-identified patent and that said Letters Patent is hereby corrected as shown below:

On the title page: Item [54] and Column 1, line 3, delete "AMINOLALICYLIC" and insert --AMINOSALICYLIC--

Signed and Sealed this

Third Day of February, 1998

Attest:

BRUCE LEHMAN

Attesting Officer

Commissioner of Patents and Trademarks